US005731204A

United States Patent [19]
Rutter et al.

[11] Patent Number: 5,731,204
[45] Date of Patent: *Mar. 24, 1998

[54] METHOD FOR REGENERATION OF CONIFEROUS PLANTS BY SOMATIC EMBRYOGENESIS EMPLOYING POLYETHYLENE GLYCOL

[75] Inventors: Mark R. Rutter, Goose Creek; Levis W. Handley, III, Charleston; Michael R. Becwar, Summerville, all of S.C.

[73] Assignee: Westvaco Corporation, New York, N.Y.

[*] Notice: The term of this patent shall not extend beyond the expiration date of Pat. No. 5,413,930.

[21] Appl. No.: 770,960

[22] Filed: Dec. 20, 1996

[51] Int. Cl.$^6$ .................................. A01H 4/00; A01H 7/00
[52] U.S. Cl. ...................... 435/430.1; 435/422; 435/430; 435/431
[58] Field of Search ........................ 435/422, 430, 435/430.1, 431

[56] References Cited

U.S. PATENT DOCUMENTS

| | | | |
|---|---|---|---|
| 4,957,866 | 9/1990 | Gupta et al. | 435/422 |
| 5,034,326 | 7/1991 | Pullman et al. | 435/422 |
| 5,036,007 | 7/1991 | Gupta et al. | 435/422 |
| 5,183,757 | 2/1993 | Roberts | 435/422 |
| 5,187,092 | 2/1993 | Uddin | 435/422 |
| 5,236,841 | 8/1993 | Gupta et al. | 435/422 |
| 5,294,549 | 3/1994 | Pullman et al. | 435/422 |
| 5,413,930 | 5/1995 | Becwar et al. | 435/422 |
| 5,491,090 | 2/1996 | Handley et al. | 435/422 |
| 5,506,136 | 4/1996 | Becwar et al. | 435/422 |
| 5,534,433 | 7/1996 | Coke | 435/431 |
| 5,563,061 | 10/1996 | Gupta | 435/422 |

OTHER PUBLICATIONS

Beardmore, T. and P. J. Charest. Black Spruce Somatic Embryo Germination and Desiccation Tolerance. I. Effects of Abscisic Acid, Cold, and Heat Treatments on the Germinability of Mature Black Spruce Somatic Embryos. *Canadian Journal of Forest Research* 25:1763–1772, 1995.

Becwar, M. R., R. Nagmani, and S. R. Wann. Initiation of embryogenic cultures and somatic embryo development in loblolly pine (*Pinus taeda*). *Canadian Journal of Forest Research* 20:810–817, 1990.

Gupta, P. K. and D. J. Durzan. Shoot multiplication from mature trees of Douglas–fir (*Pseudotsuga menziesii*) and sugar pine (*Pinus lambertiana*). *Plant Cell Reports* 4:177–179, 1985.

Hakman, I. and S. von Arnold. Plantlet regeneration through somatic embryogenesis in *Picea abies* (Norway spruce). *Journal of Plant Physiology* 121:149–158, 1985.

Hakman, I., L. C. Fowke, S. von Arnold, and T. Eriksson. The development of somatic embryos in tissue cultures initiated from immature embryos of *Picea abies* (Norway spruce). *Plant Science* 38:53–59, 1985.

Handley, L. W., M. R. Becwar, E. E. Chesick, J. E. Coke, A.P Godbey and M. R. Rutter. Research and Development of commercial tissue culture systems in loblolly pine. *Pinus taeda* L. Proceedings TAPPI 1994 Biological Sciences Symposium, Oct. 3–6, 1994. pp. 47–55. TAPPI Press 1994.

Jain, S. M., N. Dong, and R. J. Newton. Somatic embryogenesis in slash pine (*Pinus elliottii*) from immature embryos cultured in vitro. *Plant Science* 65:233–241, 1989.

Liao, Y. K. and H. V. Amerson. Slash Pine (*Pinus elliotti* Engelm.) Somatic Embryogenesis II. Maturation of Somatic Embryos and Plant Regeneration. *New Forests* 10: 165–182, 1995.

Preston, R. J. North American Trees, 4th edition. Iowa State Univ. Press, Ames. pp. 4–7, 1989.

Schenk, R. U. and A. C. Hildebrandt. Medium and techniques for induction and growth of monocotyledonous and dicotyledonous plant cell cultures. *Canadian Journal of Botany* 50:199–204, 1972.

Tautorus, T. E., L. C. Fowke, and D. I. Dunstan. Somatic embryogenesis in conifers. *Canadian Journal of Botany* 69:1873–1899, 1991.

von Arnold, S. and I. Hakman. Regulation of somatic embryo development in *Picea abies* by abscisic acid (ABA). *Journal of Plant Physiology* 132:164–169, 1988.

*Primary Examiner*—Irene Mark
*Assistant Examiner*—Janet M. Kerr
*Attorney, Agent, or Firm*—Daniel B. Reece, IV.; Terry B. McDaniel; Richard L. Schmalz

[57] ABSTRACT

This invention relates to a method for regeneration of coniferous plants. In particular, this invention relates to an improved method for producing and developing somatic embryos for somatic embryogenesis processes for plants of the genus Pinus and Pinus interspecies hybrids by including polyethylene glycol in the development media. This method is well suited for producing clonal planting stock useful for reforestation.

16 Claims, No Drawings

METHOD FOR REGENERATION OF CONIFEROUS PLANTS BY SOMATIC EMBRYOGENESIS EMPLOYING POLYETHYLENE GLYCOL

FIELD OF INVENTION

This invention relates to a method for regeneration of coniferous plants. In particular, this invention relates to an improved method for producing and developing somatic embryos for somatic embryogenesis processes for plants of the genus Pinus and Pinus interspecies hybrids by including polyethylene glycol in the development media. This method is well suited for producing clonal planting stock useful for reforestation.

BACKGROUND OF THE INVENTION

Propagation by somatic embryogenesis refers to methods whereby embryos are produced in vitro from small pieces of plant tissue or individual cells. The embryos are referred to as somatic because they are derived from the somatic (vegetative) tissue, rather than from the sexual process. Vegetative propagation via somatic embryogenesis has the capability to capture all genetic gain of highly desirable genotypes. Furthermore, these methods are readily amenable to automation and mechanization. These qualities endow somatic embryogenesis processes with the potential to produce large numbers of individual clones for reforestation purposes.

It was not until 1985 that somatic embryogenesis was discovered in conifers (Hakman et al. 1985) and the first viable plantlets were regenerated from conifer somatic embryos (Hakman and von Arnold 1985). Since 1985, conifer tissue culture workers throughout the world have pursued the development of somatic embryogenesis systems capable of regenerating plants. The goal of much of this work is to develop conifer somatic embryogenesis as an efficient propagation system for producing clonal planting stock en masse. Additionally, the embryogenic system interfaces very well with genetic engineering techniques for production of transgenic clonal planting stock of conifers.

The two most economically important conifer genera are Picea (spruce) and Pinus (pine). Those working in conifer somatic embryogenesis have found that there is a striking difference between Picea conifers and Pinus conifers as to the ease with which somatic embryogenesis can be induced and plants regenerated (Tautorus et al. 1991). In fact, when one measures the respective levels of achievement in the art of conifer somatic embryogenesis among species of these two important genera, it is clear that significantly more success has been obtained with Picea than with Pinus. Indeed, the recalcitrance of embryogenic cultures of Pinus species is well documented. This is especially true for pines commonly found in the southeastern United States (known in the industry as Southern yellow pines). Nevertheless, researchers working with Pinus species plants have recently achieved some important advances. In commonly assigned U.S. Pat. Nos. 5,413,930 and 5,506,136 (which are hereby incorporated by reference), Becwar et al. disclose multi-step methods that are able to complete the entire somatic embryogenesis regenerative process, from explant collection to planting, for historically recalcitrant Southern yellow pines (i.e., *Pinus taeda, Pinus serotina, Pinus palustris,* and *Pinus elliottii*), *Pinus rigida*, and hybrids thereof.

In commonly assigned U.S. Pat. No. 5,491,090 (which is hereby incorporated by reference), Handley et al. improved upon the above-noted processes by teaching a method which enables its practitioners to replace the semi-solid maintenance culture media taught by Becwar et al. with liquid suspension culture media.

While the methods taught in U.S. Pat. Nos. 5,413,930, 5,491,090, and 5,506,136 have achieved considerable success in both establishing embryogenic cultures of Pinus and in producing large numbers of field grown plants, these methods have proven to be somewhat limited by low embryo development frequencies experienced by different genetic families. Indeed, one of the limiting factors in achieving clonal forestry in these pines has been the inability to produce sufficient numbers of developed embryos from some of the very best genetic material and, subsequently, production of somatic embryo plants for field testing and eventual clonal deployment (Handley et al. 1995). Simply put, a major problem limiting commercial development of the above-noted methods is that they tend to exhibit relatively low embryo development frequencies in certain cell lines due to the genetic specificity of the lines.

Having a low frequency of embryo development can severely limit the potential applications of somatic embryogenesis in Pinus species for large-scale production of genetically improved conifers for the following reason. Skilled artisans in the conifer tissue culture field recognize that the use of embryogenic cultures derived from juvenile explants (e.g., zygotic embryos derived from seed) necessitate that the resulting regenerated plants be field tested prior to large scale production. Only selected genotypes which show the potential for producing significant genetic gain in such field tests will subsequently be propagated by somatic embryogenesis. It will, therefore, be necessary to screen numerous genotypes from desirable parents, initiate embryogenic cultures, cryopreserve each genetically different culture, regenerate and develop embryos and plants from each genetically different culture, field test plants from each genotype, and choose select genotypes for large scale production via somatic embryogenesis.

Low culture development frequencies pose a severe limitation for implementing this strategy; in that when few embryos are produced per gram of embryogenic callus or suspension culture cells it is almost impossible to obtain sufficient embryos for field planting. For example, embryo production at the level of around 10 to 15 embryos per clump of tissue is not commercially acceptable. Indeed, lines having embryo development rates this low are usually eliminated from testing (as it is extremely difficult to get these to produce enough embryos for a field test and later production).

As noted above, another major problem plaguing current somatic embryogenesis methods is that it has been extremely difficult to establish sufficient numbers of embryos from some of the best genetic families of Southern yellow pine. A series of experiments have shown that when propagated via the above-noted patented methods a large percentage of those embryogenic lines exhibited relatively low production numbers.

Somatic embryogenesis processes utilized with conifers (particularly the Pinus species) commonly involve seven general steps: 1) culture initiation, 2) culture maintenance, 3) embryo development, 4) embryo maturation, 5) embryo germination, 6) conversion, and 7) plant growth (field planting). The culture media utilized in the different steps are key components of effective somatic embryogenesis regeneration systems.

U.S. Pat. Nos. 5,413,930, 5,491,090, and 5,506,136 teach the use of semi-solid culture media during the embryo development step. These culture development media are generally composed of seven groups of ingredients: inorganic nutrients, vitamins, organic supplements, a carbohydrate source, phytohormones, (e.g., abscisic acid), and a gelling agent.

A significant step was made towards solving the above-noted problems when it was determined that the addition of polyethylene glycol (PEG) to development media containing either standard or very high levels of abscisic acid (ABA) resulted in a significant increase in the number of Pinus somatic embryos produced when employing the methods taught in U.S. Pat. Nos. 5,413,930, 5,491,090, and 5,506,136.

However, this improvement unveiled an additional problem. When PEG was included in the development media, the somatic embryos produced on this media failed to germinate—even after being subjected to standard germination protocols. While inclusion of PEG in development media at the levels taught in the present method significantly increased embryo production, the PEG also induced a germination block which prevented the resulting somatic embryos from germinating.

This problem was solved via the development of a novel development protocol. Under this protocol the somatic embryos are fully developed on a first development media which contains PEG. Subsequently, the somatic embryos are placed on a second development media (which does not contain PEG) and subjected to a cold treatment. The employment of these steps results in significantly increased numbers of embryos produced and, very importantly, the produced embryos can germinate into viable plants.

Therefore, an object of the present invention is to provide an improved method for the regeneration of coniferous plants by somatic embryogenesis.

Another object of the present invention is to provide an improved method for producing somatic embryos for use in somatic embryogenesis processes for plants of the genus Pinus and Pinus interspecies hybrids.

Yet another object of the present invention is to provide a method for overcoming the germination block resulting from the inclusion of polyethylene glycol in embryo development media.

A further object of the present invention is to provide an improved method for the production and germination of somatic embryos from embryogenic tissue cultures from plants of the genus Pinus and Pinus interspecies hybrids so that these embryos can converted to yield viable plants for field planting.

SUMMARY OF THE INVENTION

The above objectives are achieved by the use of an improved method for developing embryos for use in somatic embryogenesis processes employing embryogenic tissues from plants of the genus Pinus and Pinus interspecies hybrids. This method allows the practitioner to develop and germinate viable Pinus embryos from a wide range of genetic backgrounds.

This improved method teaches the addition of polyethylene glycol (PEG) to embryo development media containing either standard or very high levels of abscisic acid (ABA). While this combination of PEG and ABA significant increases the numbers of somatic embryos produced, these resulting embryos will not germinate. To correct the problem the improved method also teaches a novel development protocol which overcome this block and allow the embryos to germinate.

This method results in improved stage 3 embryo development frequencies which allow many more vigorous embryos to be obtained (which can, in turn, be successfully carried through subsequent stages of the somatic embryogenesis process) and germinated. Furthermore, the method makes it feasible to include more genotypes from families of high genetic value. Somatic plants produced from these families can be planted in clonal field tests and thereby increase the likelihood of being able to select highly productive genotypes. In addition, more genotypes can be quickly proliferated via this method for rapid production of clonal planting stock from many selected parents. The employment of previous methods often resulted in a significant number of embryogenic lines exhibiting very low (or zero) embryo development frequencies. While one may still expect that a few lines will fail to produce sufficient numbers of embryos even when using the present improved method, the overall embryo development response across lines is substantially increased.

DESCRIPTION OF THE PREFERRED EMBODIMENT

As noted above, the somatic embryogenesis process utilized with conifers (particularly the Pinus species) can be divided into seven general steps: 1) culture initiation, 2) culture maintenance, 3) embryo development, 4) embryo maturation, 5) embryo germination, 6) conversion, and 7) plant growth (field planting). The present invention improves upon the methods taught in U.S. Pat. Nos. 5,413, 930, 5,491,090, and 5,506,136 by both modifying the third step (the embryo development step) in those methods and by adding an additional step (the cold treatment step).

The improved method has a first embryo development step which comprises:

transferring at least 100 mg of the mass of embryogenic tissue (or, alternatively, at least 30 mg of the liquid embryogenic cell culture) to embryo development medium containing a sufficient amount of nutrients, a level of gelling agent selected from the group consisting of 6.0 to 12.0 g/l of agar, 1.75 to 4.0 g/l of gellan gum, 6.0 to 8.0 gl of agarose, 3.5 to 6.0 g/l of AGARGEL, and combinations thereof, 20.0 to 70.0 g/l of a sugar selected from the group consisting of glucose, maltose, sucrose, melezitose, and combinations thereof, and wherein the improvement comprises the addition of up to about 10.0 g/l of activated carbon, about 10 g/l to about 100 g/l of polyethylene glycol, about 5 mg/l to about 300 mg/l of abscisic acid, and the continued maintenance of the abscisic acid concentration; for a sufficient time under suitable environmental conditions to develop stage 3 somatic embryos.

As noted above, the improved method includes the addition of an extra step to the above-noted methods. This additional step, hereafter referred to as the second embryo development step (or cold treatment step), comprises:

transferring the stage 3 somatic embryos to a second embryo development medium containing a sufficient amount of nutrients, a level of gelling agent selected from the group consisting of 6.0 to 12.0 g/l of agar, 1.75 to 4.0 g/l of gellan gum, 6.0 to 8.0 g/l of agarose, 3.5 to 6.0 g/l of AGARGEL, and combinations thereof, 20.0 to 70.0 g/l of a sugar selected from the group consisting of glucose, maltose, sucrose, melezitose, and combinations thereof, up to about 10 g/l of activated carbon, up to about 100 mg/l of abscisic acid, and the continued maintenance of the abscisic acid concentration; for a period of about 2 to about 12 weeks at a temperature in the range of about 0° C. to about 10° C. and under suitable environmental conditions to maintain the viability of the stage 3 somatic embryos.

The present method significantly improves the embryo development by incorporating polyethylene glycol and standard to high levels of the phytohormone abscisic acid into the media utilized during the first embryo development step (and by maintaining the ABA concentration in the media). Moreover, the second embryo development step containing the cold treatment is added to overcome the germination block problem referenced above. These changes significantly increase, across a range of genotypes, the amount and number of viable embryos developed.

These development steps are employed with the remaining method steps (culture initiation, culture maintenance, embryo maturation, embryo germination, conversion, and plant growth) taught in U.S. Pat. Nos. 5,413,930 and 5,506,136 to establish improved methods for producing coniferous plants via somatic embryogenesis. To practice the improved method one follows these steps:

1. placing a suitable explant selected from the group consisting of immature zygotic embryos and megagametophytes containing immature zygotic embryos on culture initiation medium containing a sufficient amount of nutrients, 0.1 to 5.0 mg/l of auxin, 0.1 to 1.0 mg/l of cytokinin, 10.0 to 40.0 g/l of a sugar selected from the group consisting of glucose, maltose, sucrose, melezitose, and combinations thereof, and a level of gelling agent selected from the group consisting of 2.5 to 4.5 g/l of agar, 0.5 to 1.5 g/l of gellan gum, 3.0 to 5.0 g/l of agarose, 1.5 to 3.0 g/l of AGARGEL, and combinations thereof, for 2 to 14 weeks under suitable environmental conditions to grow a culture containing embryogenic tissue;

2. transferring the embryogenic tissue culture to culture maintenance medium containing a sufficient amount of nutrients, 0.1 to 5.0 mg/l of auxin, 0.1 to 1.0 mg/l of cytokinin, 10.0 to 40.0 g/l of a sugar selected from the group consisting of glucose, maltose, sucrose, melezitose and combinations thereof, and a level of gelling agent selected from the group consisting of 6.0 to 9.0 g/l of agar, 1.75 to 4.0 g/l of gellan gum, 6.0 to 8.0 g/l of agarose, 3.5 to 5.0 g/l of AGARGEL, and combinations thereof; for a sufficient amount of time under suitable environmental conditions to develop a mass of embryogenic tissue having a weight of at least 100.0 mg;

3. transferring at least 100 mg of the mass of embryogenic tissue to a first embryo development medium containing a sufficient amount of nutrients, a level of gelling agent selected from the group consisting of 6.0 to 12.0 g/l of agar, 1.75 to 4.0 g/l of gellan gum, 6.0 to 8.0 g/l of agarose, 3.5 to 6.0 g/l of AGARGEL, and combinations thereof, 20.0 to 70.0 g/l of a sugar selected from the group consisting of glucose, maltose, sucrose, melezitose, and combinations thereof, and wherein the improvement comprises the addition of up to about 10.0 g/l of activated carbon, about 10 g/l to about 100 g/l of polyethylene glycol, about 5 mg/l to about 300 mg/l of abscisic acid, and the continued maintenance of the abscisic acid concentration; for a sufficient time under suitable environmental conditions to develop stage 3 somatic embryos;

4. transferring the stage 3 somatic embryos to a second embryo development medium containing a sufficient amount of nutrients, a level of gelling agent selected from the group consisting of 6.0 to 12.0 g/l of agar, 1.75 to 4.0 g/l of gellan gum, 6.0 to 8.0 g/l of agarose, 3.5 to 6.0 g/l of AGARGEL, and combinations thereof, 20.0 to 70.0 g/l of a sugar selected from the group consisting of glucose, maltose, sucrose, melezitose, and combinations thereof, up to about 10 g/l of activated carbon, up to about 100 mg/l of abscisic acid, and the continued maintenance of the abscisic acid concentration; for a period of about 2 to about 12 weeks at a temperature in the range of about 0° C. to about 10° C. and under suitable environmental conditions to maintain the viability of the stage 3 somatic embryos;

5. separating the stage 3 somatic embryos from the cold treatment development medium and partially drying the embryos by exposing the embryos to an atmosphere having a high relative humidity for a period of about 2 to 5 weeks;

6. transferring the partially dried somatic embryos to germination medium containing a sufficient amount of nutrients, up to 10.0 g/l of activated carbon, a level of gelling agent selected from the group consisting of 6.0 to 9.0 g/l of agar, 1.75 to 3.50 g/l of gellan gum, 6.0 to 8.0 g/l of agarose, 3.5 to 5.0 g/l of AGARGEL, and combinations thereof, and 20.0 to 40.0 g/l of a sugar selected from the group consisting of glucose, maltose, sucrose, and combinations thereof, for a sufficient time under suitable environmental conditions to germinate the partially dried embryos;

7. converting the germinated embryos into acclimatized plants; and 8. field planting the acclimatized plants.

Alternatively, one may utilize the improved development steps for producing stage 3 somatic embryos with the remaining method steps (culture initiation, culture maintenance, embryo maturation, embryo germination, conversion, and plant growth) taught in U.S. Pat. Nos. 5,491,090 to create an improved method for producing coniferous plants via somatic embryogenesis. To practice the improved method one follows these steps:

1. placing a suitable explant selected from the group consisting of immature zygotic embryos and megagametophytes containing immature zygotic embryos on culture initiation medium containing a sufficient amount of nutrients, 0.1 to 5.0 mg/l of auxin, 0.1 to 1.0 mg/l of cytokinin, 5.0 to 100.0 g/l of a sugar selected from the group consisting of glucose, maltose, sucrose, melezitose, and combinations thereof, and a level of gelling agent selected from the group consisting of 2.5 to 4.5 g/l of agar, 0.5 to 1.5 g/l of gellan gum, 3.0 to 5.0 g/l of agarose, 1.5 to 3.0 g/l of AGARGEL, and combinations thereof, for 2 to 14 weeks under suitable environmental conditions to grow a culture containing embryogenic tissue;

2. transferring the embryogenic tissue culture to liquid suspension culture maintenance medium containing a sufficient amount of nutrients, 0.1 to 100.0 mg/l of auxin, 0.05 to 10.0 mg/l of cytokinin, 5.0 to 100.0 g/l of a sugar selected from the group consisting of glucose, maltose, sucrose, melezitose and combinations thereof, and about 0.1 to 10.0 g/l of activated carbon, for a sufficient amount of time under suitable environmental conditions to develop a liquid embryogenic cell culture;

3. transferring at least 30 mg of the liquid embryogenic cell culture to a first embryo development medium containing a sufficient amount of nutrients, a level of gelling agent selected from the group consisting of 6.0 to 12.0 g/l of agar, 1.75 to 4.0 g/l of gellan gum, 6.0 to 8.0 g/l of agarose, 3.5 to 6.0 g/l of AGARGEL, and combinations thereof, 20.0 to 70.0 g/l of a sugar selected from the group consisting of glucose, maltose, sucrose, melezitose, and combinations thereof, and wherein the improvement comprises the addition of up to about 10.0 g/l of activated carbon, about 10 g/l to about 100 g/l of polyethylene glycol, about 5 mg/l to about 300 mg/l of abscisic acid, and the continued maintenance of the abscisic acid concentration; for a sufficient time under suitable environmental conditions to develop stage 3 somatic embryos;

4. transferring the stage 3 somatic embryos to a second embryo development medium containing a sufficient amount of nutrients, a level of gelling agent selected from the group consisting of 6.0 to 12.0 g/l of agar, 1.75 to 4.0 g/l of gellan gum, 6.0 to 8.0 g/l of agarose, 3.5 to 6.0 g/l of AGARGEL, and combinations thereof; 20.0 to 70.0 g/l of a sugar selected from the group consisting of glucose, maltose, sucrose, melezitose, and combinations thereof, up to about 10 g/l of activated carbon, up to about 100 mg/l of abscisic acid, and the continued maintenance of the abscisic acid concentration; for a period of about 2 to about 12 weeks at a temperature in the range of about 0° C. to about 10° C. and under suitable environmental conditions to maintain the viability of the stage 3 somatic embryos;

5. separating the stage 3 somatic embryos from the cold treatment development medium and partially drying the embryos by exposing the embryos to an atmosphere having a high relative humidity for a period of about 2 to 5 weeks;

6. transferring the partially dried somatic embryos to a germination medium containing a sufficient amount of nutrients, up to 10.0 g/l of activated carbon, a level of gelling agent selected from the group consisting of 6.0 to 9.0 g/l of agar, 1.75 to 3.50 g/l of gellan gum, 6.0 to 8.0 g/l of agarose, 3.5 to 5.0 g/l of AGARGEL, and combinations thereof, and 20.0 to 40.0 g/l of a sugar selected from the group consisting of glucose, maltose, sucrose, and combinations thereof, for a sufficient time under suitable environmental conditions to germinate the partially dried embryos;

7. converting the germinated embryos into acclimatized plants; and 8. field planting the acclimatized plants.

This method is generally applicable to somatic tissue obtained from the Pinus species including, but not limited to, the following: *Pinus taeda* (loblolly pine), *P. elliottii* (slash pine), *P. palustris* (longleaf pine), *P. serotina* (pond pine), *P. echinata* (shortleaf pine), *P. clausa* (sand pine), *P. glabra* (spruce pine), *P. rigida* (pitch pine), *P. echinata* (shortleaf pine), *P. nigra* (Austrian pine), *P. resinosa* (red pine), *P. sylvestris* (Scotch pine), *P. banksiana* (jack pine), *P. virginiana* (Virginia pine), *P. radiata* (Monterey pine), *P. contorta* (shore pine), *P. contorta latifolia* (lodgepole pine), *P. ponderosa* (ponderosa pine), *P. leiophylla* (Chihuahua pine), *P. jeffreyi* (Jeffrey pine), and *P. engelmannii* (Apache pine), *P. strobus* (eastern white pine), *P. monticola* (western white pine), and *P. lambertiana* (sugar pine), *P. albicaulis* (whitebark pine), *P. flexilis* (limber pine), *P. strobiformis* (southwestern white pine), *P. caribaea* (Caribbean pine), *P. patula* (Mexican weeping pine), *P. tecumumanii* (Tecun Uman pine), *P. maximinoi*, *P. oocarpa* (Ocote Pine) and *P. chiapensis* (Mexican White pine). In addition, the current invention is specifically applicable to interspecies hybrids of the above mentioned pines including *Pinus rigida*×*P. taeda*, *P. serotina*×*P. taeda*, and reciprocal crosses.

It is preferred to utilize the present method with Southern yellow pines, Pinus rigida, and hybrids thereof. Those skilled in the art recognize that several species of pine indigenous to the Southeastern United States are closely related and hybridize naturally. Taxonomically this group of pines is referred to as "Southern yellow pines" and includes *Pinus taeda*, *P. serotina*, *P. palustris*, and *P. elliottii* (Preston 1989).

An essential element of the present invention is the incorporation of abscisic acid (ABA) into the first embryo development media formulation used to develop stage 3 somatic embryos from conifer embryogenic cell cultures. A suitable level of ABA for use in improving the embryo development media for the methods taught in U.S. Pat. Nos. 5,413,930, 5,491,090, and 5,506,136 is in the range of from about 5 to about 300 milligrams per liter (mg/l) of medium. The preferred ABA level is in the range of from about 125 mg/l to about 250 mg/l.

Yet another essential element of the present invention is the maintenance of the ABA levels in the first embryo development media. The preferred method of maintaining the ABA concentration is to transfer the tissues containing the developing embryos onto fresh development media containing an amount of abscisic acid equal to or greater than the amount present in the initial development medium. However, it is also possible to add additional ABA directly to the initial embryo development medium as needed in order to maintain the desired concentrations.

The use of ABA during the cold treatment step is optional. If ABA is included in the second embryo development media (during cold treatment), a suitable level for such ABA is in the range of up to about 100 mg/l of medium. Where ABA is utilized during the cold treatment step, the ABA levels in the embryo development media must be maintained (i.e., not be allowed to decrease over time).

Another essential element of the present invention is the use of polyethylene glycol (PEG) in the first embryo development step. That is, PEG is incorporated into the media formulations used to develop stage 3 somatic embryos from conifer embryogenic cell cultures, but not in the second development media (used during the cold treatment step). A suitable level of PEG for use in improving the embryo development media for the methods taught in U.S. Pat. Nos. 5,413,930, 5,491,090, and 5,506,136 is from about 10 to about 100 grams per liter (g/l) of medium. The preferred PEG level is in the range of about 50 g/l to about 80 g/l.

This combination of PEG and ABA proved effective both with and without the presence of activated carbon in the embryo development media employed during both embryo development steps. When employed, a suitable level of activated carbon for use in improving the embryo development media for the methods taught in U.S. Pat. Nos. 5,413,930, 5,491,090, and 5,506, 136 is in the range of up to about 10.0 grams per liter (g/l) of medium. The preferred activated carbon level is in the range of about 0.5 g/l to about 5.0 g/l.

In addition to the PEG and the ABA, the embryo development media also requires sufficient amounts of nutrients to allow the culture to remain viable. However, the present method is not limited to any single culture nutrient medium formulation. For example, four common basal culture media formulations which are suitable for use in the present method are listed in Table I below. However, it should be understood that any nutrient media commonly used in Pinus somatic embryogenesis will be suitable for use with this invention.

TABLE I

Formulations Of Basal Culture Media

| COMPONENT | DCR[a] | SH[b] | sdWV5[c] | MSG[d] |
|---|---|---|---|---|
| | \multicolumn{4}{c}{CONCENTRATION, mg/l} | | | |
| INORGANIC SALTS | | | | |
| $NH_4NO_3$ | 400.00 | — | 700.00 | — |
| $KNO_3$ | 340.00 | 2500.00 | 259.00 | 100.00 |
| $Ca(NO_3)_2.4H_2O$ | 556.00 | — | 963.00 | — |
| $MgSO_4.7H_2O$ | 370.00 | 400.00 | 1850.00 | 370.00 |
| $KH_2PO_4$ | 170.00 | — | 270.00 | 170.00 |
| $NH_4H_2PO_4$ | — | 300.00 | — | — |
| $CaCl_2.2H_2O$ | 85.00 | 200.00 | — | 440.00 |
| KCl | — | — | 1327.00 | 745.00 |
| KI | 0.83 | 1.00 | 0.83 | 0.83 |
| $H_3BO_3$ | 6.20 | 5.00 | 31.00 | 6.20 |
| $MnSO_4.H_2O$ | 22.30 | 10.00 | 15.16 | 16.90 |
| $ZnSO_4.7H_2O$ | 8.60 | 1.00 | 8.60 | 8.60 |
| $Na_2MoO_4.2H_2O$ | 0.25 | 0.10 | 0.25 | 0.25 |
| $CuSO_4.5H_2O$ | 0.25 | 0.20 | 0.25 | 0.03 |
| $CoCl_2.6H_2O$ | 0.03 | 0.10 | 0.03 | 0.03 |
| $NiCl_2.6H_2O$ | 0.03 | — | — | — |
| $FeSO_4.7H_2O$ | 27.80 | 15.00 | 27.80 | 27.80 |
| $Na_2EDTA$ | 37.30 | 20.00 | 37.30 | 37.30 |
| VITAMINS, AMINO ACIDS | | | | |
| Nicotinic acid | 0.50 | 0.5 | 0.50 | 0.50 |
| Pyridoxine.HCl | 0.50 | 0.5 | 0.50 | 0.10 |
| Thiamine.HCl | 1.00 | 1.00 | 1.00 | 0.10 |
| Glycine | 2.00 | 2.00 | 2.00 | — |

[a]According to Gupta and Durzan (1985).
[b]According to Schenk and Hildebrandt (1972).
[c]According to Coke (1996).
[d]According to Becwar et al. (1990).

Suitable media for use in improving the embryo development steps for the methods taught in U.S. Pat. Nos. 5,413,930, 5,491,090, and 5,506,136 contain from about 20.0 to about 70.0 grams per liter (g/l) of a sugar selected from the group consisting of glucose, maltose, sucrose, melezitose, and combinations thereof. The preferred sugar content for the media is from about 1 5.0 to about 40.0 g/l.

Suitable media for use in improving the embryo development step for the methods taught in U.S. Pat. Nos. 5,413,930, 5,491,090, and 5,506,136 contain a level of gelling agent selected from the group consisting of 6.0 to 12.0 g/l of agar, 1.75 to 4.0 g/l of gellan gum, 6.0 to 8.0 g/l of agarose, 3.5 to 6.0 g/l of AGARGEL® (an agar/gellan gum mixture commercially available from Sigma Chemical Company), and combinations thereof.

A suitable embryo development period for use in the first embryo development step for the methods taught in U.S. Pat. Nos. 5,413,930, 5,491,090, and 5,506,136 lasts for about 3 to 18 weeks; with the preferred period being about 8 to 12 weeks. Suitable cold treatment periods for the second embryo development step last for about 2 to 12 weeks; with the preferred period being about 3 to 6 weeks. The present method allows embryos to be developed from embryogenic tissue which has been cryopreserved.

A number of terms are known to have differing meanings when used in the literature. The following definitions are believed to be the ones most generally used in the field of botany and are consistent with the usage of the terms in the present specification.

A "cell line" is a culture that arises from an individual explant.

"Clone" when used in the context of plant propagation refers to a collection of individuals having the same genetic makeup.

"Corrosion cavity" is the cavity within the megagametophyte tissue of conifers formed by the growth and enlargement of the zygotic embryos.

"Conversion" refers to the acclimatization process that in vitro derived germinating somatic embryos undergo in order to survive under ex vitro (nonaxenic) conditions, and subsequent continued growth under ex vitro conditions.

An "embryogenic culture" is a plant cell or tissue culture capable of forming somatic embryos and regenerating plants via somatic embryogenesis.

"Embryogenic tissue", in conifers, is a mass of tissue and cells comprised of very early stage somatic embryos and suspensor-like cells embedded in a mucilaginous matrix. The level of differentiation may vary significantly among embryogenic conifer cultures. In some cases, rather than containing well-formed somatic embryos, the embryogenic tissue may contain small, dense clusters of cells capable of forming somatic embryos. This has also been referred to as "embryogenic suspensor masses" by some researchers and is also called "embryogenic callus" in some of the conifer somatic embryogenesis literature; but most researchers believe it is not a true callus.

An "established" embryogenic liquid suspension culture is considered to be any culture that grows and can be maintained in a viable embryogenic state.

An "explant" is the organ, tissue, or cells derived from a plant and cultured in vitro for the purpose of starting a plant cell or tissue culture.

"Extrusion" is the process by which zygotic embryos and/or embryogenic tissue derived from zygotic embryos emerges or extrudes from the corrosion cavity of the megagametophyte of conifer seeds via the opening in the micropylar end, when placed in culture.

"Field planting" is the establishment of laboratory, greenhouse, nursery, or similarly grown planting stock under field conditions.

"Genotype" is the genetic constitution of an organism; the sum total of the genetic information contained in the chromosomes of an organism.

"Germination" is the emergence of the radicle or root from the embryo.

"Initiation" is the initial cellular proliferation or morphogenic development that eventually results in the establishment of a culture from an explant.

"Megagametophyte" is haploid nutritive tissue of the conifer seed, of maternal origin, within which the conifer zygotic embryos develop.

"Micropyle" is the small opening in the end of the conifer seed where the pollen tube enters the ovule during fertilization, and where embryogenic tissue extrudes from the megagametophyte during culture initiation.

"Nutrients" are the inorganics (e.g., nitrogen), vitamins, organic supplements, and carbon sources necessary for the nourishment of the culture.

A "plantlet" is a small germinating plant derived from a somatic embryo.

"Regeneration", in plant tissue culture, is a morphogenic response to a stimuli that results in the production of organs, embryos, or whole plants.

"Stage 1 embryos" are small embryos consisting of an embryonic region of small, densely cytoplasmic cells subtended by a suspensor comprised of long and highly vacuolated cells.

"Stage 2 embryos" are embryos with a prominent (bullet shaped) embryonic region that is more opaque and with a more smooth and glossy surface than stage 1 embryos.

"Stage 3 embryos" are embryos with an elongated embryonic region with small cotyledons visible.

"Somatic embryogenesis" is the process of initiation and development of embryos in vitro from somatic cells and tissues.

A "somatic embryo" is an embryo formed in vitro from vegetative (somatic) cell by mitotic division of cells. Early stage somatic embryos are morphologically similar to immature zygotic embryos; a region of small embryonal cells subtended by elongated suspensor cells. The embryonal cells develop into the mature somatic embryo.

A "suspension culture" is a culture composed of cells suspended in a liquid medium, usually agitated on a gyrotory shaker. An embryogenic suspension culture in conifers is usually composed of early stage somatic embryos with well formed suspensor cells and dense cytoplasmic head cells that float freely in the liquid medium.

A "suspensor cell" is an extension of the base of the embryo that physically pushes the embryo into the megagametophyte in conifer seeds and is comprised of elongated and highly vacuolated cells. In a somatic embryo these elongated cells are clustered in rows and extend from the base of the dense cytoplasmic cells at the head or apex.

A "zygotic embryo" is an embryo derived from the sexual fusion of gametic cells.

The following examples are provided to further illustrate the present invention and are not to be construed as limiting the invention in any manner.

EXAMPLE 1

The methods claimed in U.S. Pat. Nos. 5,413,930 and 5,506,136 were followed in this example. However, evaluations were conducted to determine what effect the addition of polyethylene glycol to the embryo development media might have on the production of stage 3 somatic embryos.

Immature seed cones were collected from several different loblolly pine (*Pinus taeda* L.) sources located in Westvaco's S.C. coastal breeding orchards near Charleston, S.C. The seed cones were collected when the dominant zygotic embryo was at the precotyledonary stage of development. Using the classification system of von Arnold and Hakman (1988), the dominant zygotic embryo at this stage is referred to as being at stage 2; that is, an embryo with a prominent embryonic region with a smooth and glossy surface, subtended by elongated suspensor cells which are highly vacuolated. However, zygotic embryos at an earlier stage of development (stage 1) may also be used effectively to initiate embryogenic cultures.

Seed cones were harvested from selected trees, placed in plastic bags and stored at 4° C. until used for culture initiation. If the cones were stored for more than two weeks at 4° C., they were aired and dried out weekly (placed at 23° C., ambient laboratory conditions for 2–3 hours) to prevent growth of fungi on the surface of the cones and concomitant deterioration of seed quality.

For culture initiation, intact seeds removed from seed cones were surface sterilized by treatment in a 10 to 20% commercial bleach solution (equivalent of a 0.525% to 1.050% sodium hypochlorite solution) for 15 minutes followed by three sterile water rinses (each of five minutes duration). Seeds were continuously stirred during the sterilization and rinsing process.

Megagametophytes containing developing zygotic embryos were used as the explant for culture initiation. The seed coats of individual seeds were cracked open under a laminar-flow hood with the use of a sterile hemostat. The intact megagametophyte (which contains the developing zygotic embryos) was removed from the opened seed coat with forceps. Tissues attached to the megagametophyte, such as the megagametophyte membrane and the nucellus, were removed from the megagametophyte and discarded. The megagametophyte was placed on culture medium (longitudinal axis of megagametophyte parallel to the surface of culture medium) with forceps. The micropyle end of the megagametophyte was placed in contact with (but not submerged in) the culture medium.

Basal salt mixtures which have proven effective for culture initiation include the basal salts formulations listed in Table I. (The complete formulations of the media used in the Examples are listed in Table II.). The pH of the medium was adjusted to 5.8 with KOH and HCl prior to autoclaving at 110 kPa (16 psi) and 121° C. for 20 minutes. Aqueous stock solutions of L-glutamine were filter sterilized and added to warm (about 60° C.) medium prior to pouring the medium into culture dishes. Approximately 20 ml of medium was poured into 100×15 mm sterile plastic petri dishes.

TABLE II

Composition Of Initiation and Maintenance Media Commonly Used In The Examples

| COMPONENT | Initiation Medium $DCR_1$ | Semi-Solid Maintenance Medium $DCR_1$ | Liquid Maintenance Medium $DCR_2$ |
|---|---|---|---|
| Basal medium[a] | DCR | DCR | DCR |
| | CONCENTRATION (g/l) | | |
| Inositol | 0.50 | 0.50 | 0.50 |
| Casein hydrolysate | 0.50 | 0.50 | 0.50 |
| Sucrose | 30.00 | 30.00 | 30.00 |
| GELRITE[b] | 1.25 | 2.00 | 0 |
| Activated Carbon | 0 | 0 | 0.5 |
| | CONCENTRATION (mg/l) | | |
| Auxin[c] | 3.00 | 3.00 | 3.00 |
| Cytokinin[d] | 0.50 | 0.50 | 0.50 |

[a]Refer to Table I for composition of basal medium.
[b]GELRITE ® (gellan gum manufactured by Merck, Inc.)
[c]2,4-dichlorophenoxyacetic acid (2,4-D).
[d]$N^6$-benzylaminopurine [or $N^6$-benzyladenine (BAP)].

After megagametophyte explants were placed in culture, the perimeter of the dishes were sealed with two wraps of PARAFILM® (manufactured by American Can Co.). The dishes were incubated in the dark at a constant temperature of 23° C. After about 7 to 21 days, embryogenic tissue extruded from the micropyle of the megagametophyte explants. After 28 days in culture embryogenic tissue was removed from responsive megagametophyte explants and moved to a new position on the same culture dish, or the embryogenic tissue was transferred to a new culture dish containing the same culture medium as used for initiation. Each individual culture derived from an individual megagametophyte explant was kept separate and assigned a cell line identification code.

Cultures were maintained on semi-solid medium, i.e., $DCR_1$ (Table II) by subculturing masses of embryogenic tissue every 14 to 2 1 days to fresh medium. Culture maintenance conditions were the same as for culture initiation, except that the gelling agent levels contained in the culture maintenance media were increased.

At the end of a two to three week period of subculturing on DCR maintenance medium, masses of embryogenic tissue (about 200 mg each) were transferred to a $MSG_1$ development medium (see Table III below) containing about 11 mg/l of ABA and no activated carbon. All cultures were incubated at 23° C. in the dark. It is preferred that the cultures be incubated in the dark rather than light condition. The embryogenic tissue was transferred to fresh embryo development medium as often as needed in order to keep the concentration of ABA in the media from being reduced. After two passages on the $MSG_1$ medium, cotyledonary somatic embryos (stage 3) were visible on the surface of the embryogenic tissue. Typically, multiple harvests of cotyledonary somatic embryos were made at the end of the second and third transfers, and sometimes after the fourth transfer onto $MSG_1$ medium. Subsequently the embryogenic tissue became necrotic and produced very few, if any, cotyledonary somatic embryos on $MSG_1$ medium and the embryogenic tissue was discarded.

TABLE III

Composition of Development and Germination Media Used In The Examples

| COMPONENT | Development Medium 1 $MSG_1$ | Development Medium 2 $MSG_2$ | Germination Medium $MSG_3$ |
|---|---|---|---|
| Basal medium[a] | MSG | MSG | MSG |
| CONCENTRATION (g/l) | | | |
| Ammonium nitrate | — | — | 0.80 |
| Inositol | 0.10 | 0.10 | 0.10 |
| L-glutamine | 1.45 | 1.45 | — |
| Sucrose | — | — | 30.00 |
| Maltose | 60.00 | 60.00 | — |
| GELRITE[b] | 2.00 | 2.00 | 2.00 |
| Activated carbon | 0–1.25 | 0–1.25 | 5.00 |
| PEG[c] | 0–100.00 | — | — |
| CONCENTRATION (mg/l) | | | |
| ABA[d] | 11–150 | 21 | — |

[a]Refer to Table I for composition of basal medium.
[b]GELRITE ® (gellan gum manufactured by Merck, Inc.).
[c]Polyethylene glycol (molecular weight of 4000).
[d]Abscisic acid.

The effect of the level of polyethylene glycol (PEG) contained in the first development medium on the production of harvestable stage 3 somatic embryos (SEs) of *Pinus taeda* were evaluated using four different embryogenic culture genotypes (listed as A, B, C, and D), and the results recorded in Table IV below. The mean values listed in Table IV are based on the results obtained using three culture plates for each different PEG level and culture line.

TABLE IV

Effect Of Polyethylene Glycol Levels On Somatic Embryos

| PEG Levels | Mean Number of Stage 3 SEs Harvested Per Culture Plate | | | |
|---|---|---|---|---|
| (%) | A | B | C | D |
| 0 | 0 | 4 | 4 | 15 |
| 3 | 2 | 14 | 25 | 50 |
| 6 | 3 | 32 | 20 | 66 |
| 9 | 2 | 35 | 11 | 39 |

The results listed in Table IV clearly show that the inclusion of PEG in the embryo development media resulted in the production of significantly higher numbers of stage 3 somatic embryos. For example, embryo production was increased on these culture lines by an average of 225% when a 6% level of PEG was included in the development media.

EXAMPLE 2

The methods claimed in U.S. Pat. No. 5,491,090 were followed in this example. However, evaluations were conducted to determine what effect the addition of polyethylene glycol to the embryo development media might have on the production of stage 3 somatic embryos.

Immature seed cones were collected from several different loblolly pine (*Pinus taeda* L.) sources located in Westvaco's S.C. coastal breeding orchards near Charleston, S.C. The seed cones were collected when the dominant zygotic embryo was at the precotyledonary stage of development. Using the classification system of von Arnold and Hakman (1988), the dominant zygotic embryo at this stage is referred to as being at stage 2; that is, an embryo with a prominent embryonic region with a smooth and glossy surface, subtended by elongated suspensor cells which are highly vacuolated. However, zygotic embryos at an earlier stage of development (stage 1) may also be used effectively to initiate embryogenic cultures.

Seed cones were harvested from selected trees, placed in plastic bags and stored at 4° C. until used for culture initiation. If the cones were stored for more than two weeks at 4° C., they were aired and dried out weekly (placed at 23° C., ambient laboratory conditions for 2–3 hours) to prevent growth of fungi on the surface of the cones and concomitant deterioration of seed quality.

For culture initiation, intact seeds removed from seed cones were surface sterilized by treatment in a 10 to 20% commercial bleach solution (equivalent of a 0.525% to 1.050% sodium hypochlorite solution) for 15 minutes followed by three sterile water rinses (each of five minutes duration). Seeds were continuously stirred during the sterilization and rinsing process.

Megagametophytes containing developing zygotic embryos were used as the explant for culture initiation. The seed coats of individual seeds were cracked open under a laminar-flow hood with the use of a sterile hemostat. The intact megagametophyte (which contains the developing zygotic embryos) was removed from the opened seed coat with forceps. Tissues attached to the megagametophyte, such as the megagametophyte membrane and the nucellus, were removed from the megagametophyte and discarded. The megagametophyte was placed on culture medium (longitudinal axis of megagametophyte parallel to the surface of culture medium) with forceps. The micropyle end of the megagametophyte was placed in contact with (but not submerged in) the culture medium.

Basal salt mixtures which have proven effective for culture initiation include the basal salts formulations listed in Table I. (The complete formulations of the media used in the Examples are listed in Table II.). The pH of the medium was adjusted to 5.8 with KOH and HCl prior to autoclaving at 110 kPa (16 psi) and 121° C. for 20 minutes. Aqueous stock solutions of L-glutamine were filter sterilized and added to warm (about 60° C.) medium prior to pouring the medium into culture dishes. Approximately 20 ml of medium was poured into 100×15 mm sterile plastic petri dishes. The basal media modified for each of the culture stages are listed in Tables II and III above.

Embryogenic tissue cultures from two loblolly pine sources were initiated on semi-solid $DCR_1$ medium containing 3.0 mg/l 2,4-D, 0.5 mg/l BAP, and 0.125% GELRITE. Once cultures were extruded and subcultured, they were kept on the above medium but with the GELRITE concentration increased to 0.2%. After 10–22 months on this semi-solid maintenance medium, the callus clumps were placed in $DCR_2$ liquid maintenance medium containing 3 mg/l 2,4-D, 0.5 mg/l BAP, and 0.5 g/l activated carbon (as taught in U.S. Pat. No. 5,491,090). These were maintained by subculturing to fresh $DCR_2$ liquid medium every 1 to 2 weeks.

After 16 weeks in liquid culture, 5 lines from these two sources were plated on GELRITE-solidified $MSG_1$ development media in which the levels of PEG, ABA, and activated carbon were varied in order to assess the ability of the respective cultures to develop high quality harvestable stage 3 embryos. A sterile 90 mm sterile NITEX nylon membrane disk (#3–35/16XX, commercially available from Tetko, Inc.) was placed in a sterile Buchner funnel. Three 40 mm nylon disks were placed on top of this larger nylon disk in the funnel equidistant from one another but not touching. One ml of suspension culture cells and medium were pipetted onto each of the 40 mm disks. The liquid medium was suctioned from the cells using a mild vacuum. Each 40 mm nylon disk with cells was removed from the Buchner funnel and placed on GELRITE solidified $MSG_1$ (see Table III) in 100×25 mm plastic petri dishes. Dishes were incubated in a dark growth chamber at 23° C. The nylon disks were then transferred to new petri dishes containing fresh medium every 3 weeks. There were 12 disks of suspension culture cells from each line placed on each treatment medium.

Between weeks 6 and 12, stage 3 embryos were counted and those deemed suitable for germination were harvested. The results are listed in Table V below.

TABLE V

Effect Of Polyethylene Glycol Levels On Somatic Embryos

| Harvest # | Development Media* | | | | | | Total |
|---|---|---|---|---|---|---|---|
|  | 1 | 2 | 3 | 4 | 5 | 6 |  |
| Harvest 1 | 95 | 647 | 136 | 426 | 780 | 1291 | 3375 |
| Harvest 2 | 731 | 944 | 313 | 1054 | 1135 | 2008 | 6185 |
| Harvest 3 | 186 | 314 | 162 | 499 | 74 | 697 | 1882 |
| Sum | 1012 | 1905 | 611 | 1929 | 1989 | 3996 | 11442 |

*Media Formulations:
1 - MSG basal, no PEG, 21 mg/l of ABA, no activated carbon.
2 - MSG basal, 7% PEG, 21 mg/l of ABA, no activated carbon.
3 - MSG basal, no PEG, 125 mg/l of ABA, no activated carbon.
4 - MSG basal, 7% PEG, 125 mg/l of ABA, no activated carbon.
5 - MSG basal, no PEG, 125 mg/l of ABA, 1.25 g/l of activated carbon.
6 - MSG basal, 7% PEG, 125 mg/l of ABA, 1.25 g/l of activated carbon.

The results listed in Table V show that the inclusion of PEG in the embryo development media resulted in the production of significantly higher numbers of stage 3 somatic embryos when compared to the number of embryos produced on media not containing PEG.

EXAMPLE 3

Germination of the stage 3 somatic embryos produced in Examples 1 and 2 from both the PEG-containing embryo development media mad the control media (which did not contain PEG) was attempted utilizing the methods claimed in U.S. Pat. Nos.5,413,930, 5,491,090, and 5,506,136. First, the harvested stage 3 somatic embryos were transferred with forceps to sterile NITEX nylon membranes and were then partially dried by exposing the embryos to an atmosphere having a high relative humidity for a period of about 2 to 5 weeks. The partially dried somatic embryos were then placed horizontally on the surface of $MSG_3$ medium. The medium was in 100×15 mm sterile plastic petri plates. Typically, about 16 to 25 somatic embryos were placed in each plate. The perimeter of plates were wrapped twice with PARAFILM. Plates with embryos were incubated in the dark at 23° C. in an attempt to initiate germination. After about 10 to 14 days a number of the embryos produced using the control (no PEG) development media proceeded to elongate to approximately 1 to 2 cm. At this time the germination process had begun, with the emergence of the radicle (root) on some somatic embryos. Plates with the germinating somatic embryos were then transferred to a 16-hour fluorescent light and 8-hour dark photoperiod at 25° C.

However, no germination occurred in those somatic embryos which had been produced on PEG-containing development media. These unexpected results showed that the use of PEG at the noted levels in culture media throughout the development step somehow caused the resulting stage 3 somatic embryos to exhibit a germination block. To overcome this germination block, an additional cold treatment step was added to the somatic embryogensis process (see Examples 4–6 below).

EXAMPLE 4

A number of the stage 3 somatic embryos from Example 2 which had been cultured on development media containing PEG (i.e., Groups 2, 4, and 6) were divided into two samples. The first sample was immediately subjected to the partial drying protocol and the germination protocol taught in Example 3 above.

The second sample, however, was subjected instead to a cold treatment protocol prior to undergoing the partial drying and germination steps. This cold treatment step consisted of culturing the somatic embryos in the dark on a second development medium ($MSG_2$, Table III) which contained 21 mg/l of ABA, no PEG, and no activated carbon, for four weeks at a temperature of 4° C.

After the respective samples had undergone the germination protocol for about 8 weeks, the somatic embryos were examined for germination. The results were tallied and are listed in Table VI below.

TABLE VI

Effect of Cold Treatment on the Germination of Somatic Embryos

| Development Media* | % GERMINATION | |
|---|---|---|
|  | No Cold Treatment | Cold Treatment |
| 2 | 0 | 46 |
| 4 | 0 | 42 |
| 6 | 0 | 34 |
| Average % | 0 | 41 |

*Media Formulations:
2 - MSG basal, 7% PEG, 21 mg/l of ABA, no activated carbon.
4 - MSG basal, 7% PEG, 125 mg/l of ABA, no activated carbon.
6 - MSG basal, 7% PEG, 125 mg/l of ABA, 1.25 g/l of activated carbon.

The PEG block is clearly illustrated by the fact that no germination occurred in those somatic embryos which had not undergone the cold treatment. However, germination was achieved in a significant number of those somatic embryos produced on PEG-containing development media when these embryos were subjected to the additional cold treatment step.

EXAMPLE 5

Immature seed cones were collected from a hybrid pine (*Pinus rigida*×*Pinus taeda*) seed source located in Westvaco's S.C. coastal breading orchard near Charleston, S.C. The seed cones were collected when the dominant zygotic embryo was at the precotyledonary stage of development. Using the classification system of von Arnold and Hakman (1988), the dominant zygotic embryo at this stage is referred to as being at stage 2; that is, an embryo with a prominent embryonic region with a smooth and glossy surface, subtended by elongated suspensor cells which are highly vacuolated. However, zygotic embryos at an earlier stage of development (stage 1) may also be used effectively to initiate embryogenic cultures.

Seed cones were harvested from selected trees, placed in plastic bags and stored at 4° C. until used for culture initiation. If the cones were stored for more than two weeks at 4° C., they were aired and dried out weekly (placed at 23° C., ambient laboratory conditions for 2–3 hours) to prevent growth of fungi on the surface of the cones and concomitant deterioration of seed quality.

For culture initiation, intact seeds removed from seed cones were surface sterilized by treatment in a 10 to 20% commercial bleach solution (equivalent of a 0.525% to 1.050% sodium hypochlorite solution) for 15 minutes followed by three sterile water rinses (each of five minutes duration). Seeds were continuously stirred during the sterilization and rinsing process.

Megagametophytes containing developing zygotic embryos were used as the explant for culture initiation. The seed coats of individual seeds were cracked open under a laminar-flow hood with the use of a sterile hemostat. The intact megagametophyte (which contains the developing zygotic embryos) was removed from the opened seed coat with forceps. Tissues attached to the megagametophyte, such as the megagametophyte membrane and the nucellus, were removed from the megagametophyte and discarded. The megagametophyte was placed on culture medium (longitudinal axis of megagametophyte parallel to the surface of culture medium) with forceps. The micropyle end of the megagametophyte was placed in contact with (but not submerged in) the culture medium.

Basal salt mixtures which have proven effective for culture initiation include the basal salts formulations listed in Table I. (The complete formulations of the media used in the Examples are listed in Table II.). The pH of the medium was adjusted to 5.8 with KOH and HCl prior to autoclaving at 110 kPa (16 psi) and 121° C. for 20 minutes. Aqueous stock solutions of L-glutamine were filter sterilized and added to warm (about 60° C.) medium prior to pouring the medium into culture dishes. Approximately 20 ml of medium was poured into 100×15 mm sterile plastic petri dishes.

After megagametophyte explants were placed in culture, the perimeter of the dishes were sealed with two wraps of PARAFILM® (manufactured by American Can Co.). The dishes were incubated in the dark at a constant temperature of 23° C. After about 7 to 21 days, embryogenic tissue extruded from the micropyle of the megagametophyte explants. After 28 days in culture embryogenic tissue was removed from responsive megagametophyte explants and moved to a new position on the same culture dish, or the embryogenic tissue was transferred to a new culture dish containing the same culture medium as used for initiation. Each individual culture derived from an individual megagametophyte explant was kept separate and assigned a cell line identification code.

Cultures were maintained on semi-solid medium, i.e., $DCR_1$ (Table II) by subculturing masses of embryogenic tissue every 14 to 21 days to fresh medium. Culture maintenance conditions were the same as for culture initiation, except that the gelling agent levels contained in the culture maintenance media were increased.

After 10–22 months on this semi-solid maintenance medium, the callus clumps were placed in $DCR_2$ liquid maintenance medium containing 3 mg/l 2,4-D, 0.5 mg/l BAP, and 0.5 g/l activated carbon (as taught in U.S. Pat. No. 5,491,090). These were maintained by subculturing to fresh $DCR_2$ liquid medium every 1 to 2 weeks. After 16 weeks in liquid culture, suspension culture cells were harvested. A sterile 90 mm sterile NITEX nylon membrane disk (#3–35/16XX, commercially available from Tetko, Inc.) was placed in a sterile Buchner funnel. Three 40 mm nylon disks were placed on top of this larger nylon disk in the funnel equidistant from one another but not touching. One ml of suspension culture cells and medium were pipetted onto each of the 40 mm disks. The liquid medium was suctioned from the cells using a mild vacuum.

Three 40 mm disks were transferred to petri plates containing $MSG_1$ medium (Table III above) containing 7% PEG, 125 mg/l ABA and 1.25 g/l activated carbon. All cultures were incubated at 23° C. in the dark. The embryogenic tissue was transferred to fresh embryo development medium as often as needed in order to keep the concentration of ABA in the media from being reduced. After two passages on the $MSG_1$ medium, cotyledonary somatic embryos (stage 3) were visible on the surface of the embryogenic tissue. Typically, multiple harvests of cotyledonary somatic embryos were made at the end of the second and third passage, and sometimes after the fourth passage on $MSG_1$ medium.

The stage 3 somatic embryos were divided into two groups for testing. The first group of stage 3 somatic embryos were first partially dried in a high relative humidity environment for three weeks, then germinated directly.

The partially dried somatic embryos were placed horizontally on the surface of $MSG_3$ medium (Table III). The medium was in 100×15 mm sterile plastic petri plates. Typically, about 25 somatic embryos were placed in each plate. The perimeter of plates were wrapped twice with PARAFILM. Plates with embryos were incubated in the dark at 23° C. in an attempt to initiate germination.

The second group was subjected to a cold treatment consisting of culturing the somatic embryos in the dark on a second development medium ($MSG_2$, Table III) containing 21 mg/l ABA, no PEG and no activated carbon for four weeks at a temperature of 4° C. Afterwards, these somatic embryos were subjected to the same partial drying and germination treatments as had the first group. The results were tallied and are listed in Table VII below.

TABLE VII

Effect of Cold Treatment on the Germination of Somatic Embryos

| | % GERMINATION | |
|---|---|---|
| Development Media | No Cold Treatment | Cold Treatment |
| MSG (basal) & 7% PEG | 0.5 | 49.0 |

The PEG block allowed almost no germination to occur in those somatic embryos not subjected to the cold treatment step. However, germination was achieved in a high frequency of the somatic embryos which underwent the additional cold treatment step.

EXAMPLE 6

Immature seed cones were collected from loblolly pines located in Westvaco's S.C. coastal breeding orchard near Charleston, S.C. Following the procedures taught in Example 2 above, these seed sources were used to produce stage 3 somatic embryos from five different cell lines. These embryos were developed on development media ($MSG_1$) which contained 7% PEG, 125 mg/l ABA and 1.25 g/l activated carbon. The embryos were then split into five different groups and subsequently subjected to differing periods of cold treatment on $MSG_2$ medium with 21 mg/l ABA, but without PEG or activated carbon. Harvested embryos were partially dried, and germinated. The results were tallied and are listed in Table VIII below.

TABLE VIII

Effect of Cold Treatment on the Germination of Somatic Embryos

| Treatment Groups | Number of weeks in Cold Treatment | % Germination | % Malformed |
| --- | --- | --- | --- |
| 1 | 0 | 0 | 90 |
| 2 | 1 | 14 | 18 |
| 3 | 2 | 31 | 10 |
| 4 | 4 | 38 | 0 |
| 5 | 6 | 36 | 0 |

The results in Table VIII clearly show the effects of the germination block caused by PEG as well as the successful surmounting of that block via the employment of the cold treatment step. Malformed germinants were twisted and of a red color, typical of embryos developed on PEG medium that do not germinate.

Plants were raised from all treatments using methods described in Example 7 below and planted in the field.

EXAMPLE 7

Immature seed cones were collected from six different loblolly pine and six different hybrid pine (*Pinus rigida* × *Pinus taeda*) seed sources located in Westvaco's S.C. coastal breading orchard near Charleston, S.C. These seed sources were used to produce stage 3 somatic embryos by following the procedures taught in Examples 2, 3, and 4 above. These embryos were developed on three different development media, all of which contained 7% PEG. The stage 3 embryos were subsequently cultured in the dark on a second development medium ($MSG_2$) containing 21 mg/l of ABA (but with no PEG or activated carbon) for four weeks at a temperature of 4° C. The embryos were partially dried, germinated, and tallied (with the results listed in Table IX).

TABLE IX

Embryo Production per 0.3 ml of Embryogenic Tissue

| LINES[1] | EMBRYO DEVELOPMENT MEDIA[2] | | |
| --- | --- | --- | --- |
|  | A | B | C |
| Lob 1 | 36.6 | 96.7 | 149.2 |
| Lob 2 | 3.9 | 1.3 | 9.7 |
| Lob 3 | 59.2 | 48.3 | 99.9 |
| Lob 4 | 8.0 | 7.0 | 17.4 |
| Lob 5 | 20.5 | 17.3 | 34.8 |
| Lob 6 | 1.7 | 0.7 | 14.2 |
| P × L 1 | 61.3 | 150.3 | 121.9 |
| P × L 2 | 44.4 | 105.4 | 111.8 |
| P × L 3 | 8.8 | 17.7 | 11.4 |

TABLE IX-continued

Embryo Production per 0.3 ml of Embryogenic Tissue

| LINES[1] | EMBRYO DEVELOPMENT MEDIA[2] | | |
| --- | --- | --- | --- |
|  | A | B | C |
| P × L 4 | 68.0 | 77.0 | 116.2 |
| P × L 5 | 23.4 | 15.6 | 25.3 |
| P × L 6 | 10.6 | 5.3 | 46.9 |
| Total | 367.4 | 667.6 | 883.7 |

[1]Lob - Loblolly pine.
P × L - Pitch pine × loblolly pine hybrid.
[2]A - MSG basal, 7% PEG, 21 mg/l of ABA, no activated carbon.
B - MSG basal, 7% PEG, 125 mg/l of ABA, no activated carbon.
C - MSG basal, 7% PEG, 125 mg/l of ABA, 1.25 g/l of activated carbon.

Following the tally, several of the germinated embryos were converted into acclimatized plants and field planted via the method taught in U.S. Pat. Nos. 5,413,930, 5,491,090, and 5,506,136. When the length of the roots reached about 2 to 3 cm, the germinating plantlets from four of the loblolly lines and six of the pitch×loblolly lines were aseptically removed from the plates and planted into sterilized potting mix in MAGENTA BOXES (containers manufactured by Magenta Corp.). The boxes containing plantlets were sealed with PARAFILM and placed in a growth chamber with a 16-hour fluorescent and incandescent light and an 8-hour dark photoperiod at 23° C.

When the plantlets formed epicotyls (newly formed shoots approximately 2 to 4 cm), they were transferred to leach tubes (RAY LEACH "CONE-TAINERS"® #SSCUV manufactured by Stuewe & Sons, Inc.). Plantlets in boxes were transplanted into leach tubes containing a potting mix (2:1:2 peat:perlite:vermiculite, containing 602 g/m³ OSMO-COTE® fertilizer (18-6-12), 340 g/m³ dolomitic lime and 78 g/m³ MICRO-MAX® micronutrient mixture (manufactured by Sierra Chem. Co.). The leach tubes were placed in a greenhouse mist chamber. The environmental conditions in the mist chamber are as follows: (1) Mist was applied for 30 seconds every 30 minutes from 6:00 a.m. to 6:30 p.m., and for 30 seconds every 60 minutes from 6:30 p.m. to 6:00 a.m.; (2) Temperature was maintained at 26° to 31° C. during the day and at 18° to 20° C. at night; and (3) Ambient light was admitted through black polypropylene shade cloth (51% shade) covering the greenhouse. Supplemental light from high pressure sodium bulbs was provided to produce a total photoperiod of about 16 hours.

When the plantlets had grown to approximately 8 to 16 cm in height, trays containing the resulting plants in leach tubes were removed from the mist chamber and placed on an open bench in the greenhouse for at least two weeks for acclimatization. Subsequently, the plants in leach tube trays were moved to a shadehouse (framed structure covered with black polypropylene shade cloth) for approximately two weeks, and then to ambient outdoor conditions for an additional two weeks. Acclimatized plants were planted to a prepared field site.

Many modifications and variations of the present invention will be apparent to one of ordinary skill in the art in light of the above teachings. It is therefore understood that the scope of the invention is not to be limited by the foregoing description, but rather is to be defined by the claims appended hereto.

BIBLIOGRAPHY

Becwar, M. R., E. E. Chesick, L. W. Handley, M. R. Rutter. Method for regeneration of coniferous plants by somatic embryogenesis U.S. Pat. No. 5,413,930—issued May 9, 1995.

Becwar, M. R., E. E. Chesick, L. W. Handley, M. R. Rutter. Method for regeneration of coniferous plants by somatic embryogenesis. U.S. Pat. No. 5,506,136—issued Apr. 9, 1996.

Becwar, M. R., R. Nagmani, and S. R. Wann. Initiation of embryogenic cultures and somatic embryo development in loblolly pine (*Pinus taeda*). *Canadian Journal of Forest Research* 20:810–817, 1990.

Coke, J. E. Basal Nutrient Medium for In Vitro Cultures of Loblolly Pines. U.S. Pat. No. 5,534,433—issued Jul. 9, 1996.

Gupta, P. K. and D. J. Durzan. Shoot multiplication from mature trees of Douglas-fir (*Pseudotsuga menziesii*) and sugar pine (*Pinus lambertiana*). *Plant Cell Reports* 4:177–179, 1985.

Hakman, I. and S. von Arnold. Plantlet regeneration through somatic embryogenesis in *Picea abies* (Norway spruce). *Journal of Plant Physiology* 121:149–158, 1985.

Hakman, I., L. C. Fowke, S. von Arnold, and T. Eriksson. The development of somatic embryos in tissue cultures initiated from immature embryos of *Picea abies* (Norway spruce). *Plant Science* 38:53–59, 1985.

Handley, L. W., M. R. Becwar, E. E. Chesick, J. E. Coke, A. P. Godbey and M. R. Rutter. Research and Development of Commercial Tissue Culture Systems in Loblolly Pine. *TAPPI Journal* 78.5 (1995): 169–75.

Handley, L. W. and A. P. Godbey. Embryogenic Coniferous Liquid Suspension Cultures. U. S. Pat. No. 5,491,090—issued Feb. 13, 1996.

Preston, R. J. North American Trees, 4th edition. Iowa State Univ. Press, Ames. pp. 4–7, 1989.

Schenk, R. U. and A. C. Hildebrandt. Medium and techniques for induction and growth of monocotyledonous and dicotyledonous plant cell cultures. *Canadian Journal of Botany* 50:199–204, 1972.

Tautorus, T. E., L. C. Fowke, and D. I. Dunstan. Somatic embryogenesis in conifers. *Canadian Journal of Botany* 69:1873–1899, 1991.

von Arnold, S. and I. Hakman. Regulation of somatic embryo development in *Picea abies* by abscisic acid (ABA). *Journal of Plant Physiology* 132:164–169, 1988.

What is claimed is:

1. An improved method for reproducing plants selected from the group consisting of *Pinus taeda, Pinus serotina, Pinus palustris, Pinus elliottii, Pinus rigida*, and hybrids thereof, by somatic embryogenesis which comprises:

(a) placing a suitable explant selected from the group consisting of immature zygotic embryos and megagametophytes containing immature zygotic embryos on culture initiation medium containing a sufficient amount of nutrients, 0.1 to 5.0 mg/l of auxin, 0.1 to 1.0 mg/l of cytokinin, 10.0 to 40.0 g/l of a sugar selected from the group consisting of glucose, maltose, sucrose, melezitose, and combinations thereof, a gelling agent selected from the group consisting of 2.5 to 4.5 g/l of agar, 0.5 to 1.5 g/l of gellan gum, 3.0 to 5.0 g/l of agarose, and combinations thereof, for 2 to 14 weeks under suitable environmental conditions to grow a culture containing embryogenic tissue;

(b) transferring the embryogenic tissue culture to culture maintenance medium containing a sufficient amount of nutrients, 0.1 to 5.0 mg/l of auxin, 0.1 to 1.0 mg/l of cytokinin, 10.0 to 40.0 g/l of a sugar selected from the group consisting of glucose, maltose, sucrose, melezitose, and combinations thereof, and a gelling agent selected from the group consisting of 6.0 to 9.0 g/l of agar, 1.75 to 4.0 g/l of gellan gum, 6.0 to 8.0 g/l of agarose, and combinations thereof, for a sufficient time under suitable environmental conditions to develop a mass of embryogenic tissue having a weight of at least about 100.0 mg;

(c) transferring at least 100.0 mg of the mass of embryogenic tissue to a first embryo development medium containing a sufficient amount of nutrients, a gelling agent selected from the group consisting of 6.0 to 12.0 g/l of agar, 1.75 to 4.0 g/l of gellan gum, 6.0 to 8.0 g/l of agarose, and combinations thereof, 20.0 to 70.0 g/l of a sugar selected from the group consisting of glucose, maltose, sucrose, melezitose, and combinations thereof, and wherein the improvement comprises the addition of up to about 10.0 g/l of activated carbon, about 10.0 g/l to about 100.0 g/l of polyethylene glycol, about 5.0 mg/l to about 300.0 mg/l of abscisic acid, and the continued maintenance of the abscisic acid concentration at said level; for a sufficient time under suitable environmental conditions to develop stage 3 somatic embryos;

(d) transferring the stage 3 somatic embryos to a second embryo development medium containing a sufficient amount of nutrients, a gelling agent selected from the group consisting of 6.0 to 12.0 g/l of agar, 1.75 to 4.0 g/l of gellan gum, 6.0 to 8.0 g/l of agarose, and combinations thereof, 20.0 to 70.0 g/l of a sugar selected from the group consisting of glucose, maltose, sucrose, melezitose, and combinations thereof, up to about 10.0 g/l of activated carbon, up to about 100.0 mg/l of abscisic acid, and the continued maintenance of the abscisic acid concentration at said level; for a period of about 2 to about 12 weeks at a temperature in the range of about 0° C. to about 10° C. and under suitable environmental conditions to maintain the viability of the stage 3 somatic embryos;

(e) separating the stage 3 somatic embryos from the development medium and partially drying the embryos by exposing the embryos to an atmosphere having a high relative humidity for a period of about 2 to 5 weeks;

(f) transferring the partially dried somatic embryos to germination medium containing a sufficient amount of nutrients, up to 10.0 g/l of activated carbon, a gelling agent selected from the group consisting of 6.0 to 9.0 g/l of agar, 1.75 to 3.50 g/l of gellan gum, 6.0 to 8.0 g/l of agarose, and combinations thereof, and 20.0 to 40.0 g/l of a sugar selected from the group consisting of glucose, maltose, sucrose, and combinations thereof, for a sufficient time under suitable environmental conditions to germinate the partially dried embryos;

(g) converting the germinated embryos into acclimatized plants; and (h) field planting the acclimatized plants.

2. The method of claim 1 wherein the first embryo development medium contains from about 50 g/l to about 80 g/l of polyethylene glycol.

3. The method of claim 1 wherein the first embryo development medium contains from about 125 mg/l to about 250 mg/l of abscisic acid.

4. The method of claim 1 wherein the abscisic acid concentrations in the embryo development media are continually maintained over time by again transferring the embryogenic tissue at least once to fresh embryo development media containing an amount of abscisic acid which is at least equal to the amount of abscisic acid present in the first embryo development medium.

5. The method of claim 1 wherein the abscisic acid concentrations in the embryo development media are continually maintained over time by adding additional abscisic acid to the embryo development media.

6. The method of claim 1 wherein the embryo development media contain from about 0.5 g/l to about 5.0 g/l of activated carbon.

7. The method of claim 1 wherein the embryogenic tissue has been cryopreserved.

8. The method of claim 1 wherein the stage 3 somatic embryos are maintained on the second embryo development medium for a period of about 3 to about 6 weeks at a temperature in the range of about 0° C. to about 10° C.

9. An improved method for reproducing plants selected from the group consisting of Pinus taeda, Pinus serotina, Pinus palustris, Pinus elliottii, Pinus rigida, and hybrids thereof, by somatic embryogenesis which comprises:

(a) placing a suitable explant selected from the group consisting of immature zygotic embryos and megagametophytes containing immature zygotic embryos on culture initiation medium containing a sufficient amount of nutrients, 0.1 to 5.0 mg/l of auxin, 0.1 to 1.0 mg/l of cytokinin, 5.0 to 100.0 g/l of a sugar selected from the group consisting of glucose, maltose, sucrose, melezitose, and combinations thereof, a gelling agent selected from the group consisting of 2.5 to 4.5 g/l of agar, 0.5 to 1.5 g/l of gellan gum, 3.0 to 5.0 g/l of agarose, and combinations thereof, for 2 to 14 weeks under suitable environmental conditions to grow a culture containing embryogenic tissue;

(b) transferring the embryogenic tissue culture to liquid suspension culture maintenance medium containing a sufficient amount of nutrients, 0.1 to 100.0 mg/l of auxin, 0.05 to 10.0 mg/l of cytokinin, 5.0 to 100.0 g/l of a sugar selected from the group consisting of glucose, maltose, sucrose, melezitose, and combinations thereof, and about 0.1 to about 10.0 g/l of activated carbon, for a sufficient time under suitable environmental conditions to develop a liquid embryogenic cell culture;

(c) transferring at least 30.0 mg of the liquid embryogenic cell culture to embryo development medium containing a sufficient amount of nutrients, a gelling agent selected from the group consisting of 6.0 to 12.0 g/l of agar, 1.75 to 4.0 g/l of gellan gum, 6.0 to 8.0 g/l of agarose, and combinations thereof, 20.0 to 70.0 g/l of a sugar selected from the group consisting of glucose, maltose, sucrose, melezitose, and combinations thereof, and wherein the improvement comprises the addition of up to about 10.0 g/l of activated carbon, about 10.0 g/l to about 100.0 g/l of polyethylene glycol, about 5.0 mg/l to about 300.0 mg/l of abscisic acid, and the continued maintenance of the abscisic acid concentration at said level; for a sufficient time under suitable environmental conditions to develop stage 3 somatic embryos;

(d) transferring the stage 3 somatic embryos to embryo development medium containing a sufficient amount of nutrients, a gelling agent selected from the group consisting of 6.0 to 12.0 g/l of agar, 1.75 to 4.0 g/l of gellan gum, 6.0 to 8.0 g/l of agarose, and combinations thereof, 20.0 to 70.0 g/l of a sugar selected from the group consisting of glucose, maltose, sucrose, melezitose, and combinations thereof, up to about 10.0 g/l of activated carbon, up to about 100.0 mg/l of abscisic acid, and the continued maintenance of the abscisic acid concentration at said level; for a period of about 2 to about 12 weeks at a temperature in the range of about 0° C. to about 10° C. and under suitable environmental conditions to maintain the viability of the stage 3 somatic embryos;

(e) separating the stage 3 somatic embryos from the development medium and partially drying the embryos by exposing the embryos to an atmosphere having a high relative humidity for a period of about 2 to 5 weeks;

(f) transferring the partially dried somatic embryos to germination medium containing a sufficient amount of nutrients, up to 10.0 g/l of activated carbon, a gelling agent selected from the group consisting of 6.0 to 9.0 g/l of agar, 1.75 to 3.50 g/l of gellan gum, 6.0 to 8.0 g/l of agarose, and combinations thereof, and 20.0 to 40.0 g/l of a sugar selected from the group consisting of glucose, maltose, sucrose, and combinations thereof for a sufficient time under suitable environmental conditions to germinate the partially dried embryos;

(g) converting the germinated embryos into acclimatized plants; and (h) field planting the acclimatized plants.

10. The method of claim 9 wherein the first embryo development medium contains from about 50 g/l to about 80 g/l of polyethylene glycol.

11. The method of claim 9 wherein the first embryo development medium contains from about 125 mg/l to about 250 mg/l of abscisic acid.

12. The method of claim 9 wherein the abscisic acid concentrations in the embryo development media are continually maintained over time by again transferring the embryogenic tissue at least once to fresh embryo development media containing an amount of abscisic acid which is at least equal to the amount abscisic acid present in the first embryo development medium.

13. The method of claim 9 wherein the abscisic acid concentration in the embryo development media are continually maintained over time by adding additional abscisic acid to the embryo development media.

14. The method of claim 9 wherein the embryo development media contain from about 0.5 g/l to about 5.0 g/l of activated carbon.

15. The method of claim 9 wherein the embryogenic tissue has been cryopreserved.

16. The method of claim 9 wherein the stage 3 somatic embryos are maintained on the second embryo development medium for a period of about 3 to about 6 weeks at a temperature in the range of about 0° C. to about 10° C.

* * * * *

UNITED STATES PATENT AND TRADEMARK OFFICE
CERTIFICATE OF CORRECTION

PATENT NO. : 5,731,204
DATED : March 24, 1998
INVENTOR(S) : Mark R. Rutter, Levis W. Handley III, Michael R. Becwar It is certified that error appears in the above-indentified patent and that said Letters Patent is hereby corrected as shown below:

On the title page, first column, on the Notice line, after 5,413,930, insert --5,491,090, and 5,506,136--.

On the title page, second column, on the Primary Examiner line, delete "Mark" and substitute therefor --Marx--.

In column 9, Table I, line 8, delete "sdWV5$^c$" and substitute therefor --W$\sqrt{5}^c$--.

In column 11, line 5, delete "cell" and substitute therefor --cells--.

In column 15, line 67, start a new paragraph beginning with the sentence --The partially dried somatic . . . --.

Signed and Sealed this

Fourteenth Day of July, 1998

Attest:

BRUCE LEHMAN

Attesting Officer

Commissioner of Patents and Trademarks